United States Patent [19]

Cropper et al.

[11] Patent Number: 5,065,036
[45] Date of Patent: Nov. 12, 1991

[54] LIGHT DETECTION AND CONTROL SYSTEM

[75] Inventors: Peter R. Cropper, Sussex; Gary P. Haffenden; Jeremy K. Justice, both of East Sussex, all of England

[73] Assignee: Rhopoint Instrumentation Limited, East Sussex, England

[21] Appl. No.: 301,643

[22] Filed: Jan. 25, 1989

[30] Foreign Application Priority Data

Jan. 27, 1988 [GB] United Kingdom ............... 8801744

[51] Int. Cl.⁵ ............................................. G01N 21/86
[52] U.S. Cl. ..................................... 250/571; 356/448
[58] Field of Search ............... 250/205, 206, 559, 562, 250/571, 572; 356/445–448

[56] References Cited

U.S. PATENT DOCUMENTS

| | | | |
|---|---|---|---|
| 2,463,321 | 3/1949 | Scott | 356/448 |
| 2,471,750 | 5/1949 | Hunter | 356/448 |
| 3,449,585 | 6/1969 | Trehub | 250/205 |
| 3,462,615 | 8/1969 | Bernstein | 250/205 |
| 3,542,479 | 11/1970 | Sibalis | 250/205 |
| 3,607,623 | 9/1971 | Chappelle | 356/448 |
| 3,775,617 | 11/1973 | Dubauskas | 250/205 |
| 3,833,297 | 9/1974 | Swartz | 250/205 |
| 3,947,117 | 3/1976 | Basu et al. | 250/205 |
| 4,078,173 | 3/1978 | Fultz | 250/205 |
| 4,199,261 | 4/1980 | Tidd et al. | 356/448 |
| 4,225,245 | 9/1980 | Roiret et al. | 250/205 |
| 4,443,696 | 4/1984 | Taboada | 250/205 |
| 4,543,477 | 9/1985 | Doi et al. | 250/205 |
| 4,830,504 | 5/1989 | Frohardt et al. | 356/448 |

FOREIGN PATENT DOCUMENTS

| | | |
|---|---|---|
| 0037761 | 3/1981 | European Pat. Off. . |
| 0296596 | 6/1988 | European Pat. Off. . |
| 3242453 | 5/1984 | Fed. Rep. of Germany . |

OTHER PUBLICATIONS

Patent Abstracts of Japan, vol. 1, No. 18 (E-76) [426], Mar. 24th 1977; and JP-A-51 114 978 (Sanyo Denki) 10-09-1976-Whole Document.

Patent Abstracts of Japan, vol. 5, No. 77 (P-62) [749], May 21st 1981; and JP-A-56 22 932 (Matsushita Denki)-Whole Document.

Primary Examiner—David C. Nelms
Assistant Examiner—S. Allen
Attorney, Agent, or Firm—Darby & Darby

[57] ABSTRACT

An optical detection and control system is described for controlling the brightness of a lamp, or compensating for variations in the brightness of a lamp, such as is used, for example, in a glossmeter, hazemeter, reflectometer, colourimeter or opacity meter. In one system light is transmitted along a path from the light source (1) to a region of interest (8), means (10) are arranged to detect light scattered from the said path, and a power control (12) is coupled to the detecting means (10) to control the brightness of the light source. In another system light is transmitted along a path from the light source (1) to a region of interest (8), a first detector (10) detects light scattered from the said path, a second detector (9) detects light which has reached the region of interest (8), and a signal is produced which is proportional to the ratio of the outputs of the two detectors (8, 9).

6 Claims, 3 Drawing Sheets

Fig. 2

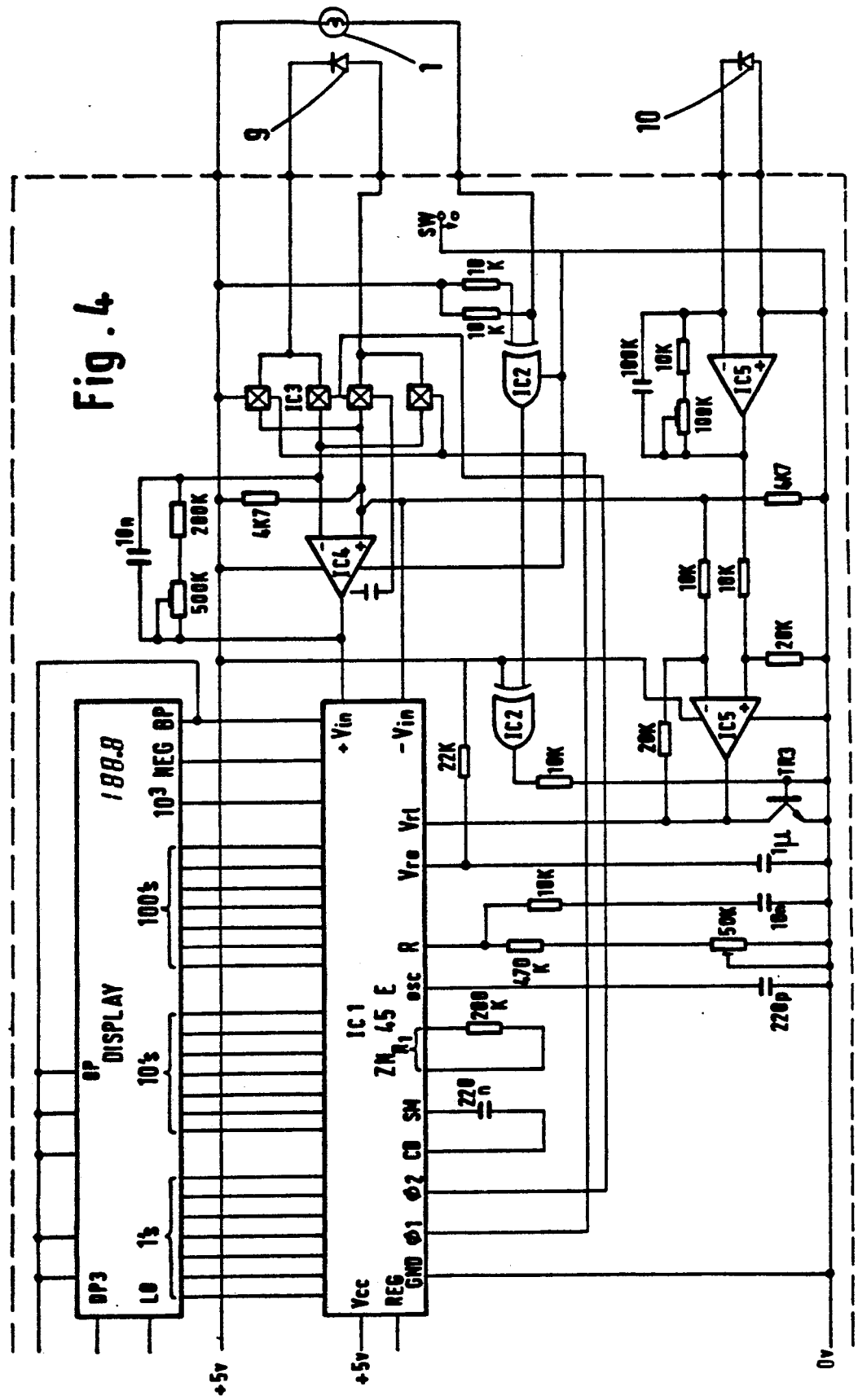

LIGHT DETECTION AND CONTROL SYSTEM

FIELD OF THE INVENTION

This application relates to an optical detection and control system. It is particularly concerned with controlling the brightness of a lamp, or compensating for variations in the brightness of a lamp, such as is used, for example, in a glossmeter, a hazemeter, a reflectometer, a colourimeter or an opacity meter.

SUMMARY OF THE INVENTION

According to the present invention there is provided a system for controlling the brightness of a light source, which comprises an optical system for transmitting light along a path from the light source to a region of interest, means for detecting light deflected from the said path, and control means coupled to the detecting means for controlling the brightness of the light source.

The invention further provides a system for compensating for variations in a light source, which comprises an optical system for transmitting light along a path from the light source to a region of interest, first detecting means for detecting light deflected from the said path and for producing a first output in response thereto, second detecting means for detecting light which has reached the region of interest and for producing a second output in response thereto, and means connected to receive the first and second outputs and for producing in response thereto a signal which is substantially independent of variations in the light source.

In preferred embodiments of the invention the above mentioned deflection of light is produced by scattering.

BRIEF DESCRIPTION OF THE DRAWINGS

In the accompanying drawings:

FIG. 4 shows in more detail the major portion of the circuit of FIG. 3.

THE DESCRIPTION OF THE PREFERRED EMBODIMENT

Figure 1:
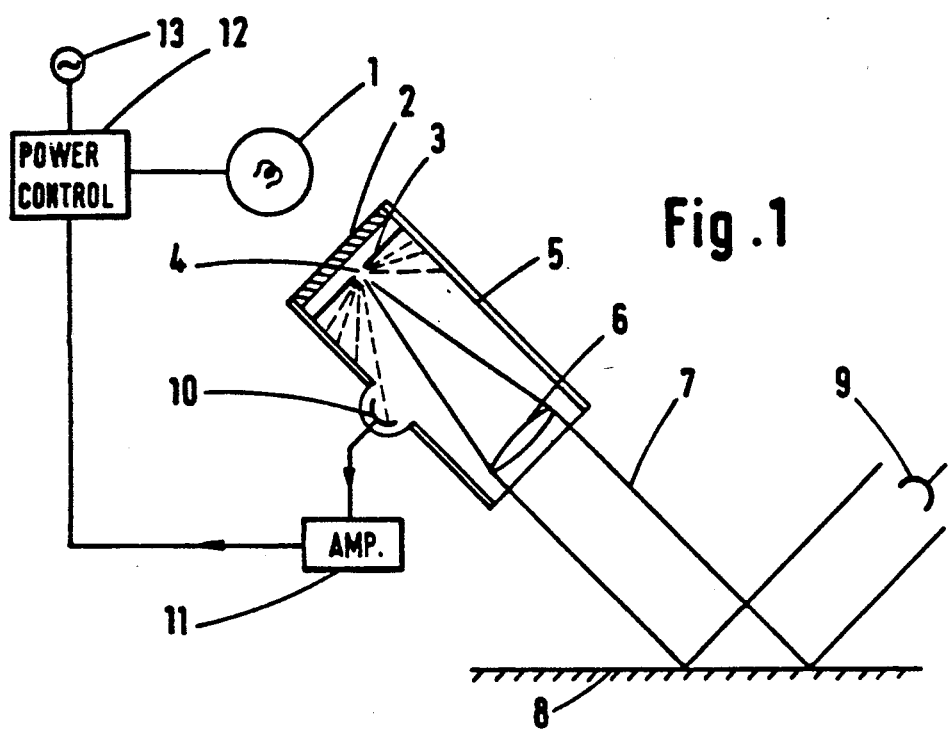
FIG. 1 shows diagrammatically an embodiment of the invention as applied to a glossmeter, in which the brightness of a lamp is varied.

In the embodiment of FIG. 1, light from a lamp 1 is incident on a diffuser 2. The lamp 1 may, for example, be a tungsten filament lamp or a quartz halogen lamp. Light passing through the diffuser strikes an image disc 3 of opaque material, in which there is formed a small slit 4. In an actual example of the image disc the slit was 1.152 mm by 0.288 mm, though it will of course be understood that other slit sizes could be used. Light is scattered from the slit 4 and enters the interior of a cylindrical tube 5 which may, for example, be of a material such as a black polyacetal resin sold under the Trade Mark DELRIN. A substantial portion of the light travels along the tube 5 to a lens 6 which forms a parallel beam of light 7. The beam 7 strikes a surface 8 whose reflective properties it is desired to investigate. Light reflected from the surface 8 is detected by a suitable detector 9, for example, a photodiode. The output of the photodiode can then be analyzed in ways which will be well known to those skilled in the art so as to provide information concerning the reflective properties of the surface 8.

The system thus far described is conventional and is the basis of known glossmeters. It has been found, however, that a problem arises in the operation of such glossmeters in that the amount of light striking the slit 4 does not remain constant, and thus spurious variations occur in the amount of light detected by the photodiode 9. Variations in the amount of light striking the slit 4 arise basically from two causes. Firstly, there are long term variations caused by the gradual change in the output of the lamp over its life. Secondly, there are changes which can be much more rapid and which are due to movement of the filament within the lamp.

In order to deal with this problem the embodiment of FIG. 1 incorporates a further photodiode 10 which is positioned in the sidewall of the tube 5. Some of the light scattered from the slit 4 falls on the photodiode 10 and the electrical output signal produced thereby is amplified by an amplifier 11 which is connected to a power control circuit 12 to which the lamp 1 and its power supply 13 are also connected. The photodiode 10 thus detects any reduction or increase in the amount of light reaching the slit 4 and the signal from the amplifier 11 to the power control circuit 12 produces a corresponding increase or decrease in the amount of power fed to the lamp 1 so as to restore the amount of light detected by the photodiode 10 to its original value. This correction can take place so rapidly as to be virtually instantaneous, and thus for practical purposes the amount of light reaching the slit can be regarded as being substantially constant with time.

Figure 2:
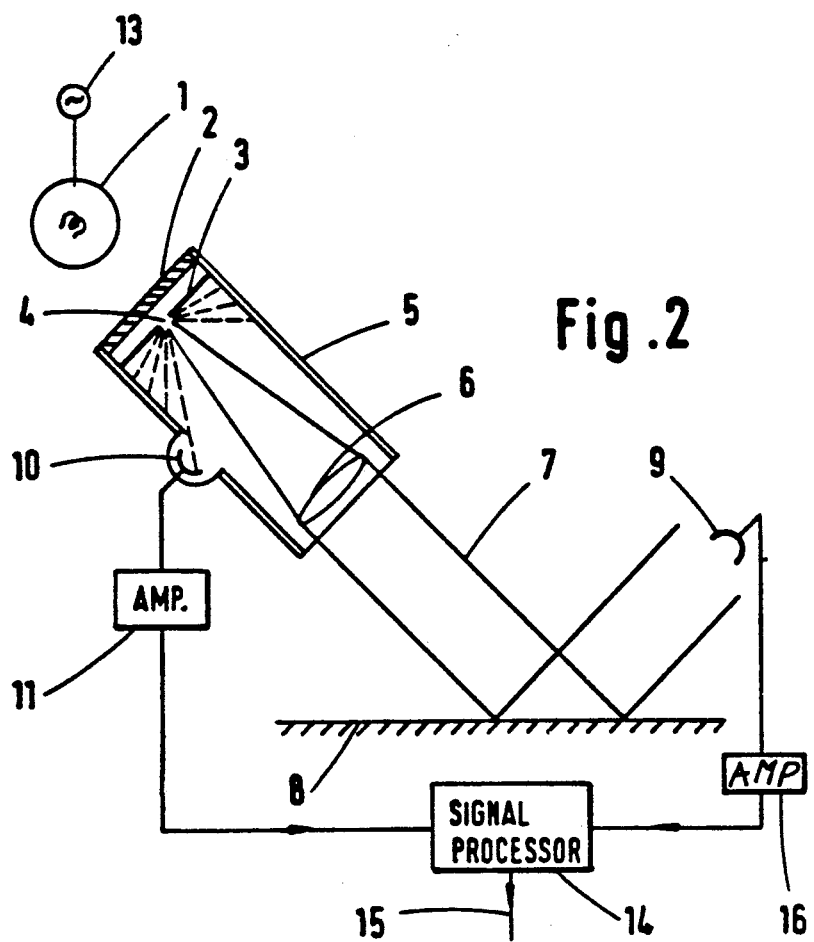
FIG. 2 shows a further embodiment of the invention as applied to a glossmeter, in which variations in the brightness of the lamp are compensated.

In the embodiment of FIG. 2 a somewhat different approach is adopted. Here the light output of the lamp 1 is not corrected, and the output signal from the amplifier 11 is fed to a signal processor 14, and the output signal from the photodiode 9 is also fed, via an amplifier 16, to the signal processor 14. This procedure at its output 15 a signal which is the ratio of the output signal of the photodiode 9 and the output signal of the photodiode 10, or is proportional thereto. Since both of these outputs are equally affected by variation in the lamp 1, their ratio is independent of variations in the lamp 1, and thus the circuit of FIG. 2 provides compensation for any variations in the lamp 1.

Figure 3:
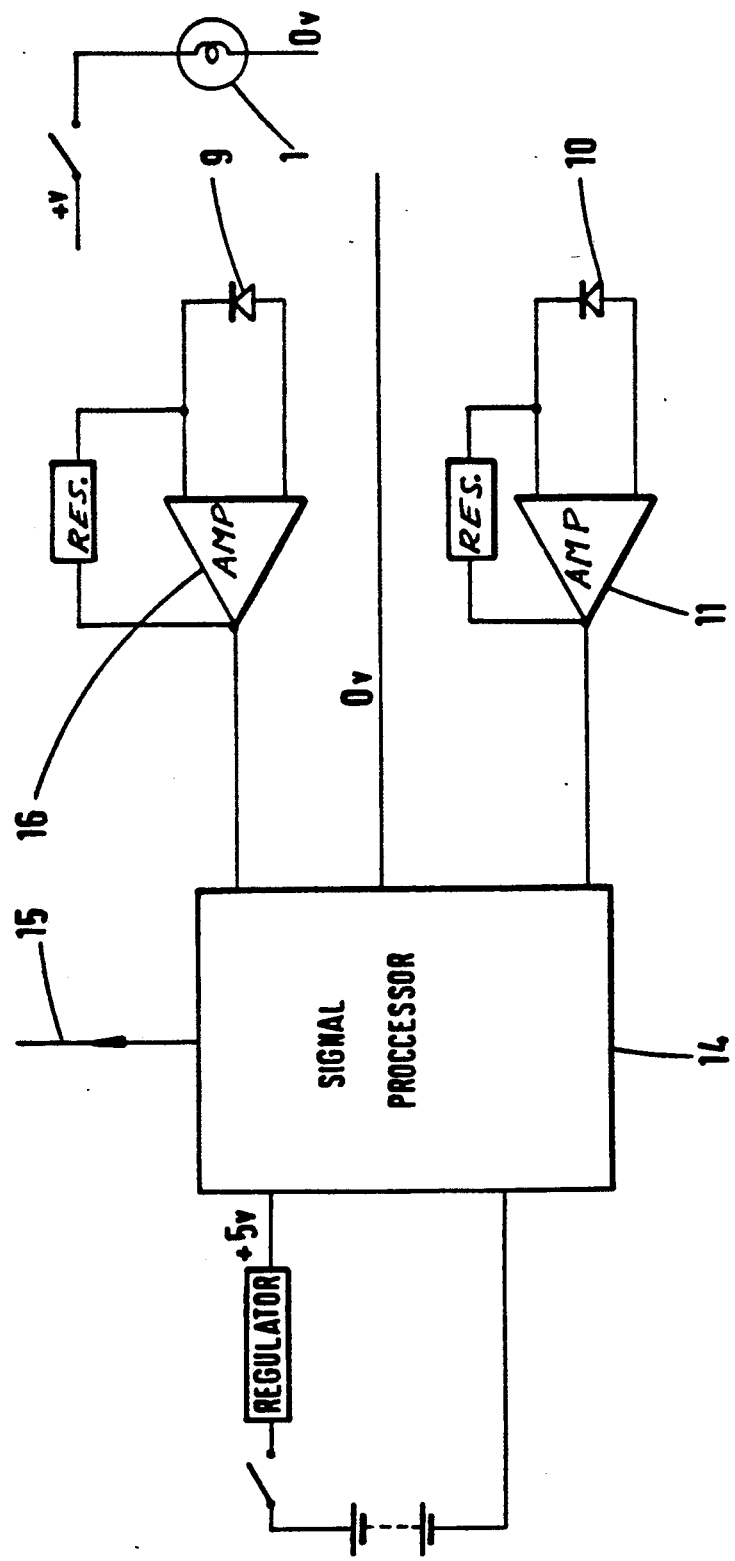
FIG. 3 shows a circuit which may be used for the embodiment of FIG. 2.

FIG. 3 shows the circuit used in the embodiment of FIG. 2, in slightly more detail. It can be seen from this that the power source used is a battery, which is connected to a voltage regulator. The output of the regulator is a stabilised voltage which is indicated as being, by way of example, five volts d.c.

FIG. 4 shows in considerably more detail the circuitry of FIG. 3, but omitting the battery and voltage regulator, which may be of entirely standard construction, and also omitting one or two incidental features which are mentioned in the description below.

The voltage produced by the photodiode 9 is supplied to the input of an amplifier IC4 via an array of four electronic switches denoted as IC3. The purpose of these switches is explained below. The amplified voltage produced at the output of amplifier IC4 is supplied by input terminals of an integrated circuit IC1 which, as explained below compares this voltage with a reference voltage. The circuit IC1 is indicated, by way of example, as being that available from Ferranti Electronics Ltd. of Oldham, Lancs, England as ZN451E. The circuit IC1 has terminals $\phi_1$ and $\phi_2$ at each of which appears a square wave signal, the signals being 180 out of phase with one another. Thus, considered together, the output of the terminals $\phi_1$ and $\phi_2$ is a square wave. This square wave is applied to the array of electronic switches IC3, so that they are alternately switched on in pairs. Thus, at any given instant either the inner two switches are conductive and the top and bottom switch are nonconductive, or vice versa. The effect of this is that the voltage from the photodiode 9 is applied alternately in opposite directions to the input terminals of the amplifier IC4. Thus, the voltage supplied by the amplifier IC4 to the circuit IC1 is alternately switched, and the circuit uses this in order to compensate for any error in the zero position.

The voltage from the photodiode 10 is amplified by the amplifier IC5, which is in two stages. The voltage appearing at the second stage of the amplifier IC5 is applied to the input Vr1 of the circuit IC1. This is the reference voltage. Logic in the circuit IC1 divides the amplitude of the voltage supplied by the amplifier IC4 by the voltage appearing at the input Vr1 to give the ratio thereof. An A/D converter within the circuit IC1 drives a display which, in this example, is a 3½ digit display, with each digit being represented in conventional 7-bar form. The most significant digit can either be 1 or is absent, and the remaining three digits can be anywhere from 0 to 9. A signal constantly applied to the input DP3 ensures that a decimal point is permanently inserted before the least significant digit. A signal from the power supply to the terminal labelled LO provides a signal if and when the voltage of the battery which provides the power supply falls below an acceptable level, and when this signal is provided the display indicates the fact. The back plane signal conventionally required for such a display is provided at the inputs BP. The remaining terminals of the display are not used.

The circuit is s arranged that when the lamp 1 is not operating the transistor TR3 is turned on via the exclusive-OR gates IC2 so that the voltage applied to the reference terminal Vr1 is then zero. For so long as the voltage at Vr1 remains zero the circuit IC1 continues to supply to the display the last value which was obtained, so that this value continues to be displayed. However, as soon as the lamp 1 is turned on, and this is done by depressing the switch SW in the direction indicated by the arrow, the gates IC2 turn the transistor TR3 off and the voltage supplied to the terminal Vr1 is then that which appears at the output of the amplifier IC5.

It will be noted that the output terminal of the amplifier IC4 is fed from the mid point between two resistors of equal value (in this case 4.7K) which are connected between the 5v and 0v lines. Thus, this terminal is held at 2.5v. This is optimum in that it allows the voltage at the -terminal to swing widely either side of 2.5v without approaching too close to zero volts. Finally, for completeness mention is made of a number of the terminals of the circuit IC1 which have not already been referred to. The terminals Vcc and REG are associated with the power supply. Power is received at the terminal Vcc, and insofar as this differs from 5 volts a feedback signal is produced at the terminal REG which controls the voltage regulator in the sense required to bring the input voltage to 5 volts. The terminal OSC is connected to ground via a capacitor the value of which determines the internal frequency of the circuit IC1 and frequency of the square wave appearing at the terminals $\phi$1 and $\phi$2. The inputs labelled CDSM have a capacitor connected across them, the value of which is determined by the internal frequency of the circuit IC1. The terminals $R_1$ have a resistor connected across them the value of which provides a coarse gain control. The terminal $R_2$ is connected to ground via circuitry which includes a variable resistor, the value of which can be adjusted to provide a fine gain control. In this context, gain control refers to the fact that the value displayed need not be the actual value of Vr1 divided by $V_{in}$ (that would be a gain of 1) but this value can be multiplied by a given factor (the gain value) to provide a displayed value which is more convenient to handle. The terminal Vro has applied to it a voltage of 1.25v, which is used for internal reference purposes.

The invention has been particularly described above with reference to a glossmeter. However, as indicated at the outset, the invention is also applicable to other instruments. A hazemeter differs from a glossmeter in that whereas in a glossmeter the light detected by the detector 9 is that which has undergone specular reflection, in a hazemeter it is that which has been reflected by an angle which deviates by a specified angle from specular reflection.

In a reflectometer, a surface of interest is illuminated at an angle which differs from 90°, and the light detected by the detector 9 is that which has been reflected at 90° to the surface. A colourimeter is similar to a reflectometer, except that the sample is illuminated with light of a specific wavelength or it is illuminated with white light and the detector 9 detects only light of a specific wavelength.

In an opacity meter, an object of interest is illuminated and the detector 9 detects light scattered therefrom.

We claim:

1. A system for compensating for variations in a light source, which comprises an optical system for transmitting light along a path from the light source to a region of interest, first detecting means for detecting light deflected from the said path, and for producing a first output in response thereto, second detecting means for detecting light which has reached the region of interest and for producing a second output in response thereto, and means connected to receive the first and second outputs and for producing in response thereto a signal which is substantially independent of variations in the light source.

2. A system according to claim 1, wherein said signal is proportional to the ratio of the second output to the first output.

3. A system according to claim 1, arranged in an instrument selected jfrom a glossmeter, a hazemeter, a reflectometer, a colourmeter and an opacity meter.

4. A system according to claim 1, wherein said light deflected from the said path is light scattered from the said path.

5. A system according to claim 4, wherein said optical system comprises a housing having at one end means arranged to receive light from the light source, and at the other end emitting light towards the region of interest, means being situated between the two ends to define an aperture from which a portion of the light is scattered to the means for detecting scattered light.

6. A system according to claim 5, wherein means for detecting scattered light is disposed in a side wall of the housing.

* * * * *